United States Patent [19]

Rooyakkers

[11] Patent Number: 4,675,012

[45] Date of Patent: Jun. 23, 1987

[54] METHOD OF FORMING AN ABSORBENT GENITALIA POUCH FOR INCONTINENT MALES

[75] Inventor: John A. Rooyakkers, Outagamie County, Wis.

[73] Assignee: Kimberly-Clark Corporation, Neenah, Wis.

[21] Appl. No.: 685,692

[22] Filed: Dec. 24, 1984

[51] Int. Cl.⁴ .............................................. A61F 5/453
[52] U.S. Cl. ................................................... 604/349
[58] Field of Search .............. 604/346, 347, 348, 349, 604/350, 351, 352, 353, 327, 396, 398, 366, 371, 389, 385 R, 323, 335; D24/51, 54, 56, 58; 2/200, 175, 198; 229/1.5 B, 115, 116; 303/907; 206/494; 220/62

[56] References Cited

U.S. PATENT DOCUMENTS

| D. 208,609 | 9/1967 | Garland . | |
|---|---|---|---|
| D. 263,169 | 2/1982 | Larko . | |
| D. 271,800 | 12/1983 | Brendling . | |
| 924,337 | 6/1909 | Frommann | 128/286 |
| 2,104,423 | 1/1938 | Hughes | 128/290 |
| 2,548,149 | 4/1951 | Fowler, Jr. . | |
| 2,822,807 | 2/1958 | Heyman | 128/159 |
| 3,035,579 | 5/1962 | Benovic | 604/353 |
| 3,172,130 | 3/1965 | Lange | D24/56 X |
| 3,200,415 | 8/1965 | Breece, Jr. | 604/347 |
| 3,707,969 | 1/1973 | Sanford | 604/347 |
| 3,724,464 | 4/1973 | Enloe | 604/385 R X |
| 3,774,610 | 11/1973 | Eckert et al. . | |
| 3,848,595 | 11/1974 | Endres | 604/385 R |
| 3,906,952 | 9/1975 | Zamist | 128/290 |
| 3,926,233 | 12/1975 | Brendling . | |
| 3,968,799 | 7/1976 | Schrading . | |
| 4,056,103 | 11/1977 | Kaczmorzyk et al. | 604/371 |
| 4,100,324 | 7/1978 | Anderson et al. | 604/374 X |
| 4,114,621 | 9/1978 | Mims | 604/398 |
| 4,445,900 | 5/1984 | Roeder | 604/389 |
| 4,453,938 | 6/1984 | Brendling . | |

FOREIGN PATENT DOCUMENTS 2142243  1/1985  United Kingdom .

Primary Examiner—Richard C. Pinkham
Assistant Examiner—Matthew L. Schneider
Attorney, Agent, or Firm—Paul A. Leipold; Donald L. Traut; Jeremiah J. Duggan

[57] ABSTRACT

The invention is generally accomplished by providing an absorbent pouch for the male genitalia that has a generally triangular opening wherein one side of the triangle is adapted to be worn flat against the upper genital region and the other two portions of the triangular opening extend into the crotch and meet behind the scrotum. The pouch extending downward from the triangular opening has sufficient capacity to comfortably contain the male genitalia, and the opening at the top is sufficient to allow air circulation. The allowance for air circulation decreases skin problems. The method for forming the device consists of folding a retangular sheet of composite material on a first fold line that is offset from the middle of the sheet. Next, the points forming the outer ends of the first fold line are folded toward each other so that they are adjacent. The newly formed edges are then folded inwardly toward each other a predetermined distance so as to form the generally triangular opening.

4 Claims, 22 Drawing Figures

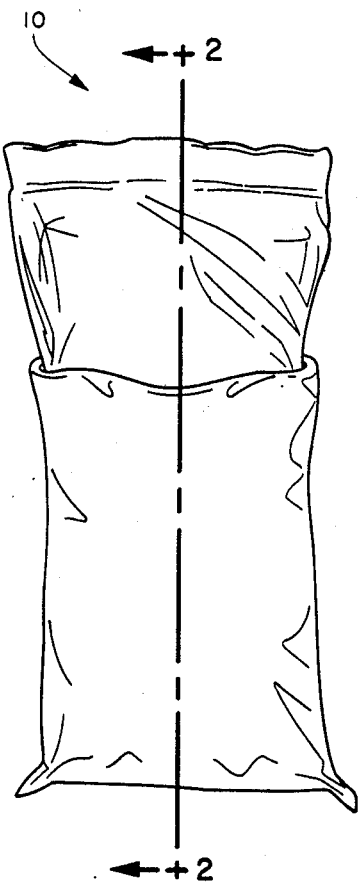
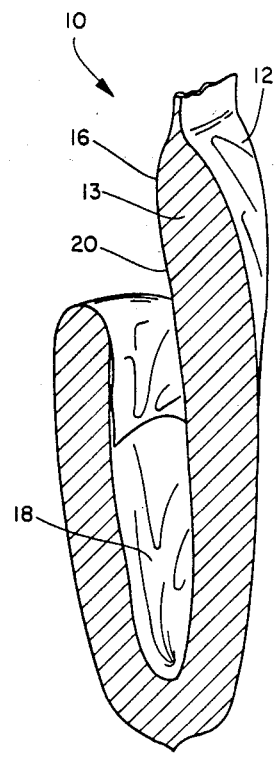
FIG. 1
(PRIOR ART)
FIG. 2
(PRIOR ART)

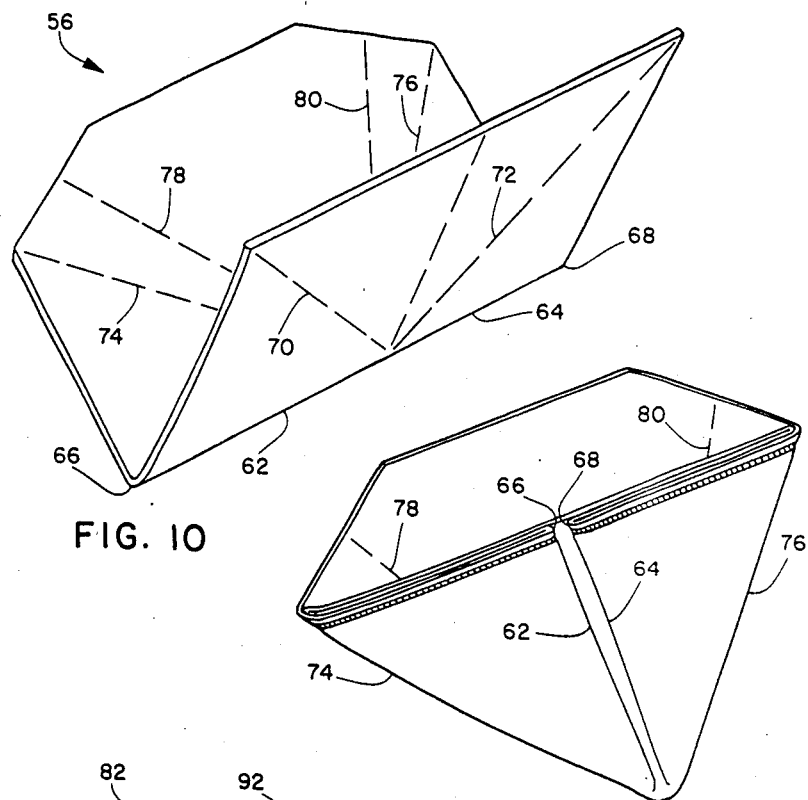
FIG. 10
FIG. 11
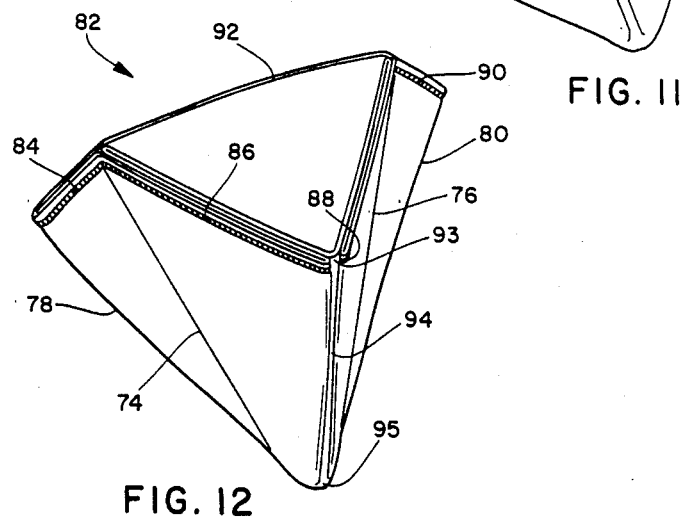
FIG. 12

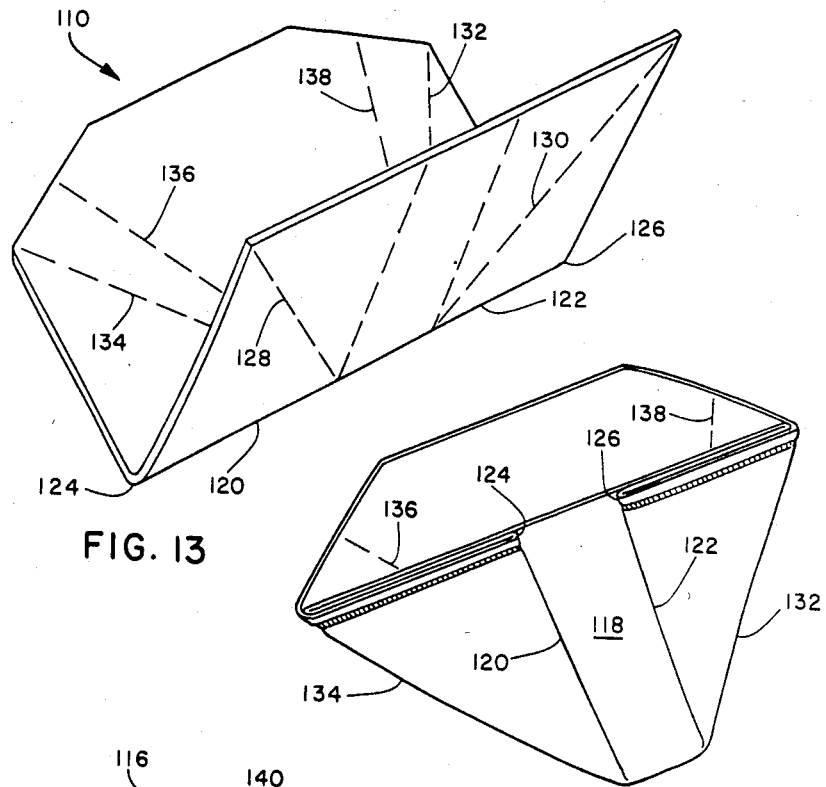
FIG. 13
FIG. 14
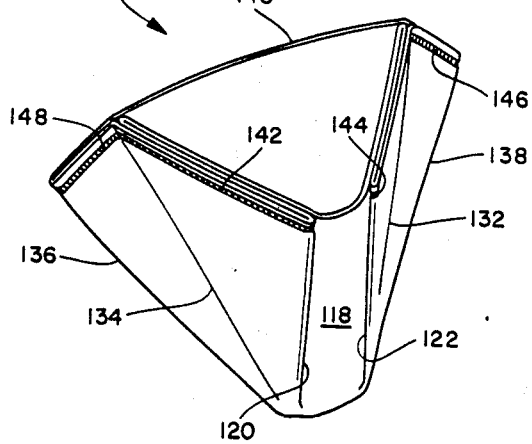
FIG. 15

METHOD OF FORMING AN ABSORBENT GENITALIA POUCH FOR INCONTINENT MALES

TECHNICAL FIELD

The present invention relates to a pouch for collection of liquids. The invention particularly relates to an absorbent-lined puch adapted to contain the male genitalia and provide for incontinence protection to the wearer.

BACKGROUND ART

It is known to form protection devices that are particularly adapted for male incontinence. The known protection devices are shaped as stocking-shaped sheaths with insertion openings facing upward. The sheath is formed with back and front walls, with the front wall extending upwards above the opening, forming a shield to provide extra protection. Such devices have the disadvantage that they may be uncomfortable and have limited capacity. Further, if the penis is substantially smaller than normal size, is retracted, or activity of the wearer caused the penis to be withdrawn, the device will provide less than satisfactory protection.

It has been proposed in U.S. Pat. No. 4,453,938 to Brendling that an incontinence guard for male users be formed. The sheath of Brendling may be large enough to contain the male genitalia. The sheath is formed of two sheets of materials that are welded at their seams and lined with a superabsorbent sheet material. This sheath has disadvantages in that the seal forming the seams must be carefully completed to prevent leakage. Further, the opening fits tightly around the genitalia, being uncomfortable even prior to use. Other male devices are those such as disclosed in U.S. Pat. No. Des. 263,169, Larko. The devices of Larko are somewhat similar to folded heavy-duty feminine pads, with the long portion intended to be toward the front and the penis inserted into the sheath formed by the fold. This device suffers from the disadvantages listed above for devices containing only the penis.

There remains a need for a device that will provide secure incontinence protection for urinary incontinent males. Devices shaped like diapers are too bulky for discreet protection. Those shaped like feminine pads are not adequate for the male as they do not provide sufficient bulk to contain the male genitalia. Devices containing only the penis are not suitable as the devices are uncomfortable, have limited capacity unless excessively bulky and are difficult to keep in place. There remains a need for a device that will contain the male genitalia, provide adequate capacity, be discreet and comfortable.

BRIEF DESCRIPTION OF THE INVENTION

An object of this invention is to provide comfortable, discreet protection for urinary incontinent men.

Another object of this invention is to provide a method of making device for urinary incontinent males that is suitable for males with retracted penises.

An additional object of this invention is to provide a method of making urinary incontinence device for males that will have low skin irritation.

A further object of this invention is to provide a method of making device for incontinent males that is low in cost to form and will not leak at the lower seals.

These and other objects are generally accomplished by providing an absorbent pouch for the male genitalia that has a generally triangular opening wherein one side of the triangle is adapted to be worn flat against the upper genital region and the other two portions of the triangular opening extend downward and backward into the crotch and meet behind the scrotum. The pouch extending downward from the triangular opening has sufficient capacity to comfortably contain the male genitalia, and the opening at the top is sufficient to allow air circulation. The allowance for air circulation decreases skin problems.

In a particularly preferred form the pouch is formed by folding of a single sheet of an impermeable backing material having fastened thereto an absorbent medium that is overlaid with a liquid-permeable member.

BRIEF DESCRIPTION OF THE DRAWINGS

FIGS. 1 and 2 illustrate a penis-containing device of the prior art.

FIGS. 10 and 11 are illustrations of folding the sheet of FIG. 8.

FIG. 12 is a pouch in accordance of the invention formed from the sheet of FIG. 8.

FIGS. 13 and 14 are illustrations of folding the sheet of FIG. 9.

FIG. 15 is the pouch of the invention formed by the folding of the sheet of FIG. 9.

MODES FOR CARRYING OUT THE INVENTION

The device of the invention has numerous advantages over prior devices. The device of the invention comfortably fits the male genitalia and is discreet as it fits flat against the front body surface. As it encloses the entire testicles and penis, it is effective even with men that have a retracted or short penis. In its preferred form the pouch of the invention has no lower seams that must be sealed in order to prevent leaks and is low in cost as it is formed from a single flat sheet. Further, the absorbent in the preferred device will not come apart when wet and sag to the bottom of the pouch. The pouch is open and loose at the top so that it permits air circulation to the genitalia. Further, the device is flexible such that is easily conforms to the shape of the person wearing it, without losing capacity or being uncomfortable. The device may be held in place by tight underclothes or by a suspension system that is discreet and low in cost. The further advantage is that the preferred device does not expose the wearer to superabsorbent materials that feel slimy and further are irritating to the skin of many persons, particularly in the sensitive genital region. These and other advantages will become apparent from the description below.

Figure 3:
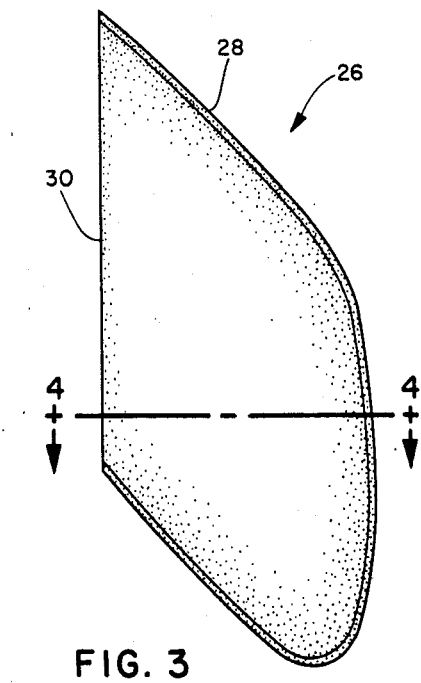
FIGS. 3, 4, and 5 illustrate a prior art device for containing the genitalia.
Figure 5:
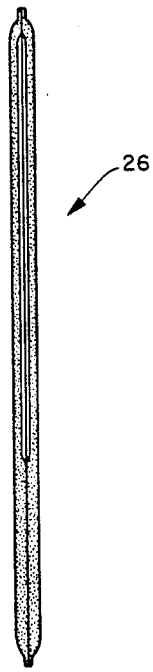
Figure 4:
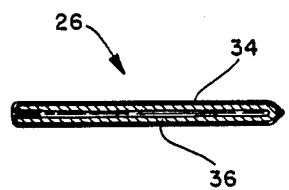

FIGS. 1 and 2 illustrate a prior art male incontinence device 10. The device is formed having an impermeable outer covering 12 absorbent inner structure 13 and permeable member on the inner surface 16. The penis is placed into portion 18. The upper portion 20 is intended to provide additional absorption, keep the penis in the container and as an aid in using the device for those with shorter penises. The device somewhat resembles a folded feminine pad. FIGS. 3, 4 and 5 are three views of a device such as that disclosed in U.S. Pat. No. 4,453,938 —Brendling—that is intended to contain the entire male genitalia. The device 26 is intended to be worn with portion 28 towards the front. It opens at 30 for the male genitals to be placed into the inside of the device 26. The device 26 is constructed of a fairly heavy gauge polymer sheet 34, lined with superabsorbent 36. As illustrated in FIG. 5, the device 26 is flat prior to use, and in use collapses onto and around the male genitalia. The device has the disadvantage that the superabsorbent tends to pool in the bottom when wet, forming a slimy uncomfortable mass.

Figure 6:
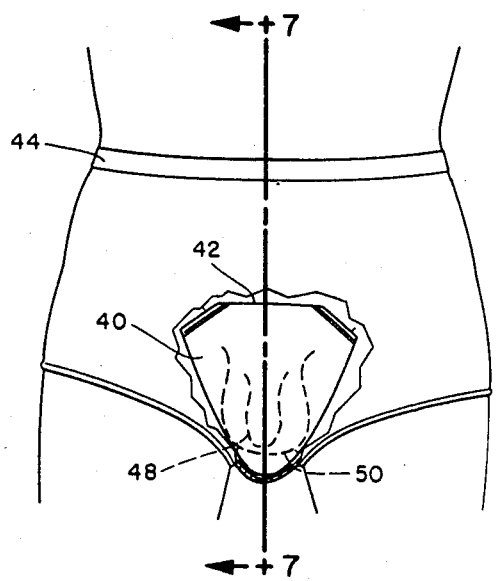
FIG. 6 is a view partially cut away of a man wearing the device of the invention.
Figure 7:
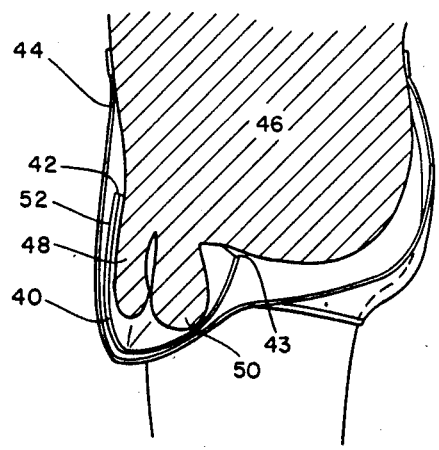
FIG. 7 is a cross-sectional view of the man of FIG. 6 long line 7—7.

As illustrated in FIG. 6, the device of the invention 40 has one side 42 of its triangular opening resting on the upper public area of the wearer. The device is held in place by a typical male brief or undergarment 44. FIG. 7, a cross-section of FIG. 6 on line 7—7, illustates that the person 46 has the garment containing the penis 48 and scrotum 50. The front portion 52 of the garment 40 is in the line of the body and not obtrusive. It is noted that the top opening of the garment 40 is open and allows air circulation.

Figure 8:
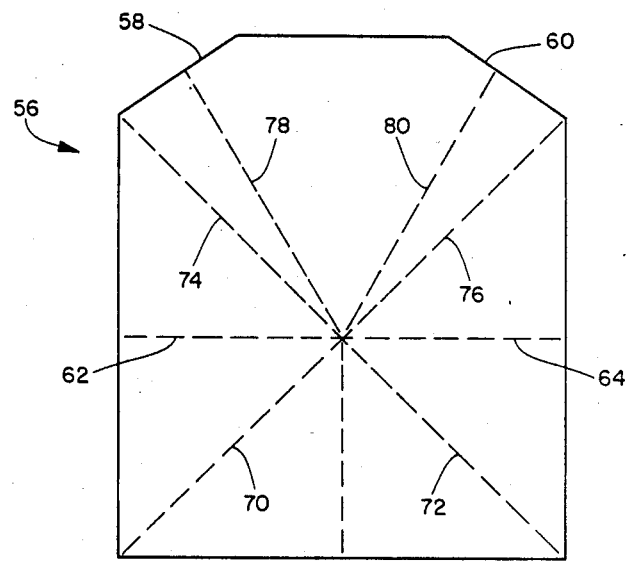
FIG. 8 is a plan view of a sheet for forming a pouch for the invention with fold lines indicated.

FIG. 8 illustrates a sheet that is suitable for forming the preferred incontinent pouch of the invention. The sheet 56 is a composite article. The sheet has an impermeable outer backing sheet. Onto this backing sheet is adhered an absorbent structure, the preferred absorbent structure being a coform material. The coform has adhered thereto a permeable body-side sheet. The body-side material generally is a spun-bonded permeable sheet. It is noted that the sheet is generally rectangular in a preferred size about 9½" by 11½" except areas 58 and 60 have been trimmed prior to folding to avoid formation of sharp ears or points on what will be the front of the garment.

FIGS. 10 and 11 illustrate folding the sheet of FIG. 8 to form the garment or pouch of FIG. 12. FIG. 10 shows sheet 56 folded on line 62 and 64. The fold line 62 and 64 is about 5" from the end of the sheet that does not have cut off areas 58 and 60. After folding on the line 62 and 64, the corners of the fold 66 and 68 are brought upward and to the center of foldlines 70, 72, 74, and 76. Foldlines 74 and 76 are then folded inward toward the center of the container on foldlines 78 and 80 to form the preferred garment of the invention 82. After the folding is complete, the upper edges of garment 82 are sealed at areas of contact 84 and 90, forming the ears of the garment. It is further sealed at the backward extending edges of the triangular opening 86 and 88. The front 92 not being a seam or of multiple thickness is not sealed. It is noted that this folding system is desirable as it leaves a garment without any seams in the bottom portion of the garment that could be a source of leaks. Further, the absorbent that is adhered to the sheet is all available for absorption of the liquid as it can be readily penetrated by the liquid even though it is concealed from contact with the body by the folds. When folds 74 and 76 are made, the fold 94 extends out to form the triangular opening of the garment. If folds 74 and 76 are not made a triangular opening garment is formed. However, the garment is of less desired structure than that formed when folds 74 and 76 are made. The garment 82 has less depth from the rear point 93 to the bottom 95 than from the front of the opening 92 to the bottom 95. The usefulness of the difference in depth is clear in FIG. 7 where the front 42 is higher than the rear point 43 when the front of the garment is generally flat against the body 46.

Figure 9:
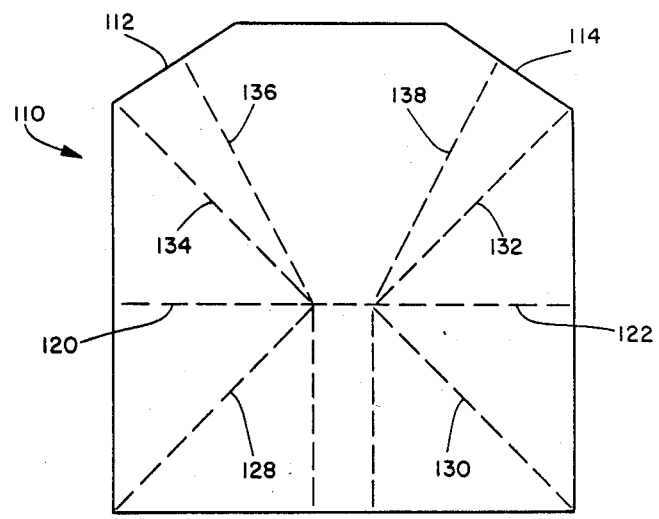
FIG. 9 is a plan view of a sheet for forming a pouch of the invention with somewhat different fold lines.

FIG. 9 is a plan view of a sheet for folding an alternative form of the pouch garment of the invention. The sheet 110 is generally rectangular of about 9.5" by 11.5 inches in a preferred form with corners cut off at 112 and 114. FIGS. 13, 14, and 15 illustrate the folding of sheet 110 to form the garment of this design 116. This garment differs in that it has a widened crotch portion 118 that some persons find more comfortable. The folding of the garment illustrated in FIGS. 13 and 14 is similar to that earlier described for FIGS. 10 and 11. The sheet 110 is originally folded along lines 120 and 122 that are somewhat offset from the center of the sheet 110. After the initial fold, corners 124 and 126 are folded upward and towards the center. However, in this instance, the corners do not meet and an open crotch portion 118 is left that will form the wider interior crotch portion of the garment 116. The folding of corners 124 and 126 is done on lines 128, 130, 132, and 134. Then folds 132 and 134 are folded inward on lines 138 and 136, forming a generally triangular opening garment with the widened crotch portion 118 making the triangle somewhat trapezoidal. Garment 116 has front portion 140 that in use will rest on the pubic region and backward extending sides 142 and 144. The garment 116 is sealed along areas of joinder 148, 142, 144, and 146 in order to form the desired permanent shape.

Figure 16:
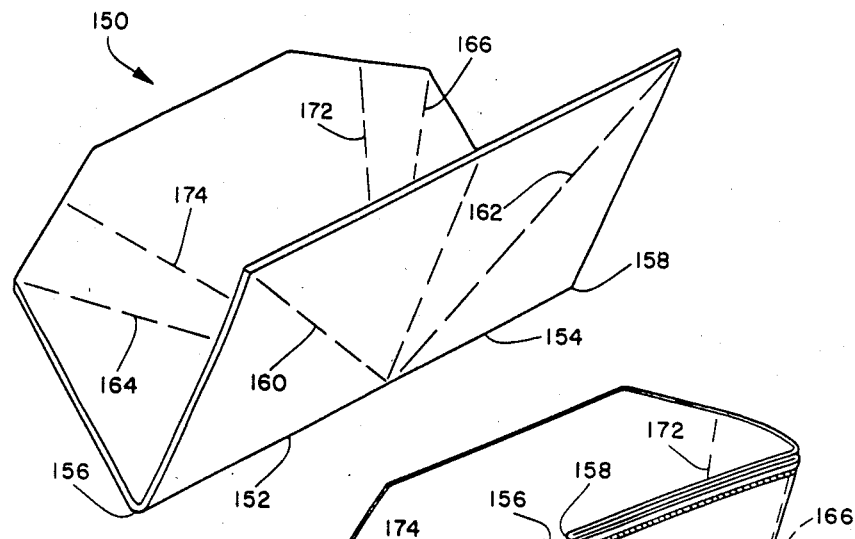
FIGS. 16 and 17 are views of an alternative folding scheme for the sheet of FIG. 8.
Figure 17:
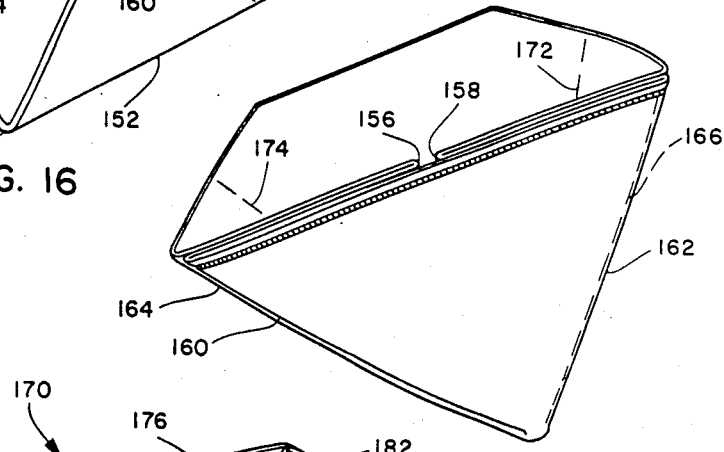
Figure 18:
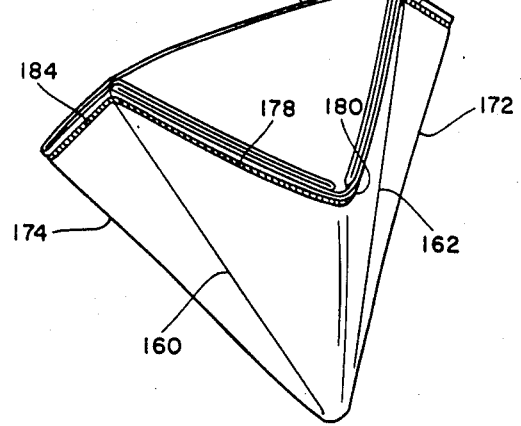
FIG. 18 is a pouch of the invention formed by the folding scheme of FIGS. 16 and 17.

FIGS. 16 and 17 illustrate an alternate fold that may be used for the garment of the invention. This fold is illustrated utilizing a sheet 150 that has fold lines similar to that of FIG. 10. Sheet 150 is folded on fold lines 152 and 154 initally the fold lines are offset from the center of the sheet 150. Then corners 156 and 158 are reversed and folded inward on fold 152 and 154. This folding inward of corners 156 and 158 leaves exposed fold lines 160, 162, 164, and 166. Corners 156 and 158 are on the interior of the garment 70. Then the folds 160 and 164 are folded inward on lines 172 and 174. Garment 170 has the front portion of the generally triangular opening 176 with backward extending portions 178 and 180. The upper edges are sealed at 184, 178, 180 and 182. The garment 170 such as formed by the fold of FIGS. 16 and 17 is not considered preferred as it is believed that the urine will have somewhat more difficulty reaching the inward folded absorbent materials in this design.

The pouch garment of the instant invention has been illustrated with these variations of folds to form the generally triangular pouch of the invention. It is, of course, possible that there are other methods of folding to form a single sheet into a triangular or trapezoidal opening pouch.

As utilized in the instant specification, the term "generally triangular" is intended to include the trapezoidal shapes such as illustrated in FIG. 15. Further, while the garments are illustrated with a generally pyramidal form, the pyramid's point in use will often fold over and an alternate fold that left a somewhat flat bottom would be suitable. It is noted that the male genitals do not end in a point, and that any bottom not uncomfortable to the male genitals would be suitable. It is theorized that the pointed bottom does have some benefit in that it provides an out-of-contact, with the genitalia, reservoir for liquids concentrated below the genitals where it is not uncomfortable.

Figure 19:
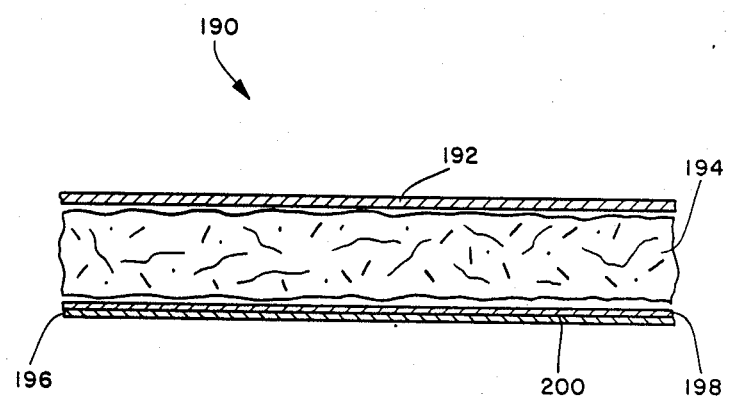
FIG. 19 is partial cross-section of a pad utilized in forming the garment of the invention.

FIGS. 19 illustrates the cross-section of a preferred pad for forming the incontinent garment of the invention. The pad 190 is formed with three layers: first, a permeable body or genitals side layer 192; second, an absorbent layer 194; and third, an impermeable backing member 196. As illustrated, the impermeable member 196 is formed of two layers: layer 198 is an impermeable polymer film, and layer 200 that is composed of a fabric covering for the impermeable polymer 198. A preferred two-layer impermeable covering material is a coextruded material in which a polymer, generally polypropylene, is extruded onto a thin, spun-bonded fabric 200. Such a material has a cloth-like feeling against the skin, yet is strong and low in cost and weight as a minimum amount of the polymer 198 is utilized.

Figure 20:
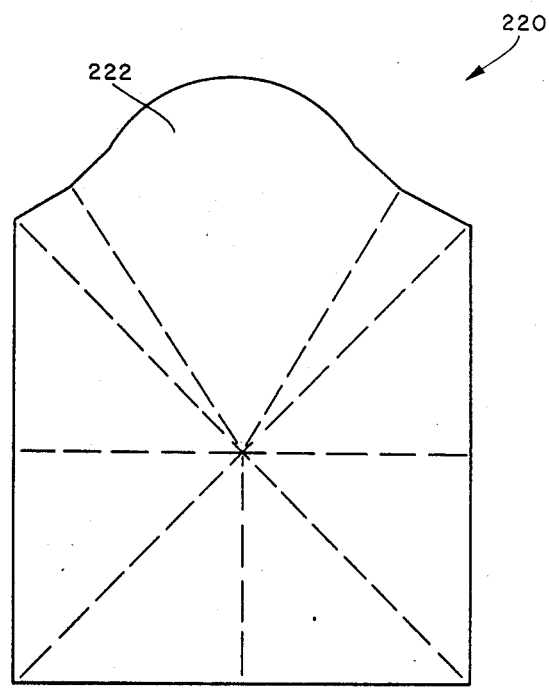
FIGS. 20 and 21 are alternate constructions of the pouch of the invention.
Figure 21:
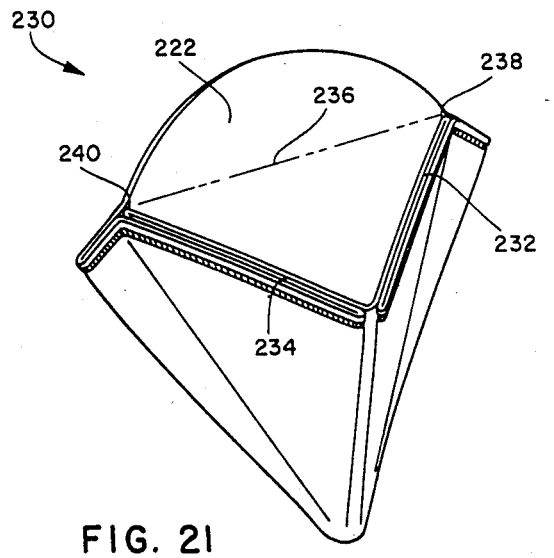

An alternate construction of the pouch of the invention is illustrated in FIGS. 20 and 21. The sheet 220 of FIG. 20 differs from the forming sheet of 8 in that a semicircular shield area 222 is formed at one end of the sheet 220. The sheet 220 is folded as illustrated in FIGS. 10, 11 and 12 to result in the pouch 230 of FIG. 21. The pouch 230 has the semicircular area 222 forming a shield 222 at the front of the pouch 230. The pouch opening is bounded by sides 232 and 234 and front phantom line 236 joining the tacked points 238 and 240. This alternative design may be particularly desirable for those instances where the wearer's penis is retracted or upturned.

A preferred permeable member 192 is a spun-bonded member. It may be the carrier sheet onto which the absorbent is laid down during formation. It is preferred that the permeable member be adhered to the absorbent for better liquid transfer and less sag. Typical of other permeable webs are carded cellulose webs or perforated polymer sheets.

A preferred absorbent is a coform structure which is an air-formed mixture of meltblown polypropylene and wood fibers. In the preferred form the three layers are adhered together. This adherence may be by adhesives, not shown, or the permeable web may be adhered to the coform by the intermingling of fibers of the coform with the web during laydown. Further, rather than adhesives, a pattern of heat-sealing also could be utilized to provide integrity to the pad. As above set forth, it is preferred that the absorbent be maintained on the backing material even when wet to avoid sagging of the garment after use.

It is also possible to utilize superabsorbent in the instant garment. The superabsorbents are polymers such as starch-derived hydrogel polymers and crosslinked acrylonitrile polymers capable of retaining large quantities of liquid by formation of gel structures. Preferred are the particulate superabsorbents such as Grain Processing Corporation Water-Lock ® J-500, sodium polyacrylate. It is preferred that the superabsorbent not be on the surface of the absorbent material facing the genitalia as some super-absorbents may cause an allergic skin rash, and in any case provide a slimy feel. It is preferred that the super-absorbent be between the backing sheet and the absorbent or be incorporated on the back of the absorbent. In a particularly preferred form, the absorbent 194 is an integrally bonded layer structure in which superabsorbent is in the layer toward the backing sheet. Such a structure is disclosed in U.S. Ser. No. 602,933 filed Apr. 23, 1983 by McFarland and Lang, which is coassigned with the instant application and hereby incorporated by reference.

While the preferred embodiments are as shown with folding from one sheet, it is also possible that a garment in accordance with the invention could be formed from separate members which are joined by sealing to form a pouch-like garment having the generally triangular opening of the invention. Such a garment could exhibit material savings over the preferred garment. However, it is not preferred as there may be seams that could be irritating to the wearer as well as a possibility of faulty seals that would provide leaks.

The size of the generally triangular-shaped opening of the pouch of the instant invention may be any size that will fit the genitalia of the wearer. Typically, the opening for an adult male and youth male is a generally equilateral triangle or trapezoid of between 7 and about 14 centimeters on a side. If measuring on a trapazoid the narrow rear portion is not measured and the other three sides are in the range specified. The size for children would be about 7 centimeters on a side of the triangular opening. Generally, the preferred size is an about 10 centimeters per side equilateral triangle for fitting the average male with comfort and providing a sufficient volume to hold urine and the genitalia.

The volume of the pouch may be any desired size to comfortably contain the penis, genitalia and urine. The suitable adult volume would be between about 275 to about 400 cc. A preferred volume would be between about 300 and about 350 cc. for the sufficient volume for absorption and genitalia but not too bulky to fit comfortably. The size for children and adolescents would require a somewhat smaller volume.

The depth of the pouch below the triangular opening may be any suitable depth that is comfortable to the wearer. Generally, the garment slopes and narrows as it descends from the opening. However, it must not narrow so fast that the genitalia are constricted. Therefore, it is generally suitable that at a depth of about 5-6½ centimeters from the rear of the triangular opening that the cross-section of the open area be about 17 to about 31 sq. cm. Note that the area is measured on a plane perpendicular to the back of the garment at a point 5 to 6½cm. down on the back wall or fold. The back may be a fold as in FIG. 12 or a wall as in FIG. 15. If the garment is folded as in the preferred structure as shown, in FIG. 12 or 15 the depth at the rearward crotch fold 118 or 94 is somewhat less than that at the front 92 or 140.

The pouch forming the garment of the invention may be held to the wearer by any suitable means. Typically, the pouch is held by a tight-fitting undergarment such as briefs or knit garments designed for the purpose. However, the garment also may be held in place by strap arrangements such as are known for feminine pads or by the placing of a line(s) or areas of pressure-sensitive adhesive on the front of the garment such as is practiced with feminine pads.

Figure 22:
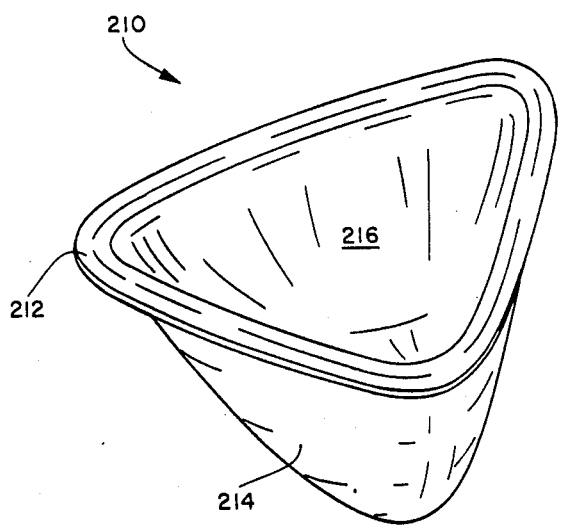
FIG. 22 is an alternate pouch of the invention formed from a soft foam sheet.

The garment has been described as formed of sheets of materials either single sheets folded in shape or sheet pieces adhered at their edges by sealing. However, the garment also could be formed by molding of a plastic material to the correct shape and then lining the molded pouch with absorbent material. Particularly preferred would be a soft, impermeable foamed sheet lined with an absorbent material such as superabsorbent containing coform. The foam may be a polyethylene-polyvinyl acetate foam sheet that is vaccum or thermally molded to shape and then has the absorbent material placed therein. Alternatively the absorbent may be bonded to the impermeable foam sheet prior to thermal molding of the foam sheet to the pouch shape. Illustrated in FIG. 22 is a molded pouch 210 in accordance with the invention. The pouch 210 has an upper molded foam lip 212 and a pouch 214 formed of impervious, molded soft foam sheet. The pouch 210 is lined with absorbent 216.

As described above, the male incontinence garment that is provided by the pouch of the instant invention provides an effective, comfortable garment at low cost. While described with specific embodiments, it is understood that other variations of the invention are possible and are intended to be included. The scope of the invention is to be limited only by the scope of the claims attached hereto.

I claim:

1. A method of forming an incontinent device comprising providing a generally rectangular composite member having an impermeable backing, a permeable cover and a layer of absorbent between said backing an said permeable cover, folding said member on a first fold line offset from the middle of said member and generally perpendicular to the long edge of said rectangle, folding the points forming outer ends of said first fold line until they are adjacent so as to form two new edges and folding the new edges inwardly toward each other a predetermined distance, thereby forming a pouched incontinent device having a generally triangular opening, the generally triangular opening being defined by three sides, two of the sides comprised three layers of said composite material and a third side comprising a single layer of said composite material, 2. The method of claim 1 further including sealing together layered edges formed at the triangular opening of said device.

3. The method of claim 2 further comprising removing two corners on one narrow end of said rectangular member, each by a single angular cut and that said first fold line is displaced a greater distance from the end having corners removed than from the other end.

4. The method of claim 3 including the folding of said member on a fold line offset from the middle of said rectangular member to points adjacent where said angular cut lines intersect the long edges of said rectangle.

* * * * *